(12) United States Patent
Abuzaid et al.

(10) Patent No.: US 12,276,582 B2
(45) Date of Patent: Apr. 15, 2025

(54) SAMPLER SYSTEM FOR WATER CONTAMINANTS

(71) Applicant: KING FAHD UNIVERSITY OF PETROLEUM AND MINERALS, Dhahran (SA)

(72) Inventors: Nabeel Saeed Fuad Abuzaid, Dhahran (SA); Muhammad Hawwa, Dhahran (SA); Mazen Khaled Nazal, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 265 days.

(21) Appl. No.: 18/151,518

(22) Filed: Jan. 9, 2023

(65) Prior Publication Data
US 2024/0230478 A1  Jul. 11, 2024

(51) Int. Cl.
G01N 1/10 (2006.01)
G01N 1/40 (2006.01)
G01N 33/18 (2006.01)

(52) U.S. Cl.
CPC ............... *G01N 1/10* (2013.01); *G01N 1/405* (2013.01); *G01N 33/18* (2013.01)

(58) Field of Classification Search
CPC ........ G01N 1/405; G01N 1/2214; G01N 1/10; G01N 5/02; G01N 33/18
USPC .............................................. 73/864, 864.71
See application file for complete search history.

(56) References Cited

U.S. PATENT DOCUMENTS

2011/0126644 A1* 6/2011 Hayes ................ G01N 1/10
                                                    210/232
2012/0222500 A1   9/2012 Riess et al.

FOREIGN PATENT DOCUMENTS

| CN | 202330069 U | 7/2012 | |
| CN | 107037193 A * | 8/2017 | ............... G01N 1/14 |
| CN | 111006901 A * | 4/2020 | |
| CN | 215727093 U | 2/2022 | |
| CN | 217424837 U | 9/2022 | |

(Continued)

OTHER PUBLICATIONS

Samuel D. Supowit, et al., "Active Sampling Device for Determining Pollutants in Surface and Pore Water—the *In Situ* Sampler for Biphasic Water Monitoring", Nature, Scientific Reports, vol. 6, Article No. 21886, Feb. 24, 2016, pp. 1-9.

*Primary Examiner* — Eric S. McCall
*Assistant Examiner* — Anthony W Megna Fuentes
(74) *Attorney, Agent, or Firm* — Oblon, McClelland, Maier & Neustadt, L.L.P.

(57) ABSTRACT

A sampler system for water contaminants. The sampler system includes an adsorptive sampler housed within a cylindrical enclosure, which has a top face, a bottom face and a cylindrical surface. The cylindrical surface of the sampler system is fluid-permeable. A cable connects the top face of the cylindrical enclosure to a flotation device. A spring connects the adsorptive sampler to the bottom face of the cylindrical enclosure. The adsorptive sampler includes a housing having a cavity and an adsorptive material disposed inside the cavity. The housing is attached to the spring and includes a front face and a back face. The spring is a cantilever in the form of a rigid film, wherein the rigid film is connected to the bottom face of the cylindrical enclosure along a flat edge of the rigid film.

20 Claims, 5 Drawing Sheets

(56) References Cited

FOREIGN PATENT DOCUMENTS

CN 115420552 A * 12/2022

* cited by examiner

SAMPLER SYSTEM FOR WATER CONTAMINANTS

BACKGROUND

Technical Field

The present disclosure is directed to water sampling for quality monitoring and contaminant detection, and particularly, to a sampler system for detecting a contaminant in an aqueous solution and determining a contaminant concentration.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Generally, water pollution leads to potential risks to fish as well as to fish-consuming wildlife and humans. Therefore, monitoring water contamination to protect both ecosystems and public health is imperative. As such, the need for measuring contaminant concentration has been leading to the development of water sampling methodologies for the determination of a dissolved contaminant mass in water. Known samplers include a sampler enclosure having an adsorbent disposed therein. The sampler is held in place within a water body at certain location by a support, such as a cable, a buoy, or a rigid arm. Particularly, the sampler is placed at a strategic location in water to have the fluid come into contact with the adsorbent, and thereby adsorb the pollutants. If the water comes in contact with the adsorbent under natural fluid forces, then the process is a passive sampling process. If the water is forced into the adsorbent of the sampler by pumping, then the process is an active sampling process. In both sampling processes, samplers are collected after a predetermined time period, analyzed in the laboratory to measure ion exchange, and specify pollutant nature and concentration. Thus, an environment specialist is able to establish baseline concentrations from the collected pollutants, determine locations of polluting sources, and identify pollutant migration and distribution routes.

Samplers, generally, help in minimizing the potential of environmental and public health damage. Further, sampling processes help in short-term, rapid environmental assessments, as well as in long-term monitoring processes to prevent catastrophic environmental events. Both active and passive sampling processes are vital in achieving these goals. Generally, the active sampling process has certain advantages, such as a faster sampling rate and the collection of a bigger amount of pollutants, over the passive sampling process. Further, the active sampling process is more efficient than the passive sampling process, though the active sampling process is more expensive than the passive sampling process. However, the active sampling process involves energy consumption for getting contaminants adsorbed onto the adsorbent of the sampler. Therefore, a need remains to develop a sampling process having the efficiency advantages of the active sampling process with the economic value of the passive sampling process.

Accordingly, it is one object of the present disclosure to provide a sampling methodology that has the advantages of the active sampling process without consuming external pumping energy for fluid pumping. It is also an object of the present disclosure to develop an inexpensive sampling process having an economic value being the same as the passive sampling process.

SUMMARY

In an exemplary embodiment, a sampler system for water contaminants is described. The sampler system includes an adsorptive sampler housed within a cylindrical enclosure. The cylindrical enclosure has a top face, a bottom face and a cylindrical surface. At least the cylindrical surface of the sampler system is fluid-permeable. The sampler system further includes a cable connecting the top face of the cylindrical enclosure to a flotation device. The sampler system further includes a spring connecting the adsorptive sampler to the bottom face of the cylindrical enclosure. The adsorptive sampler comprises a housing having a cavity and an adsorptive material disposed inside the cavity. The housing is attached to the spring and includes a front face and a back face.

In some embodiments, the fluid-permeable cylindrical surface is a screen or a mesh and the adsorptive material is at least one selected from the group consisting of activated carbon, silica gel, zirconia, titania, alumina, zeolite, and ion-exchange resins.

In some embodiments, the spring is a cantilever in the form of a rigid film. The rigid film is connected to the bottom face of the cylindrical enclosure along a flat edge of the rigid film.

In some embodiments, the adsorptive sampler is attached to at least one surface of the rigid film by the back face and the adsorptive sampler is positioned distal to the bottom face of the cylindrical enclosure.

In some embodiments, the housing of the adsorptive sampler is in the form of a cylinder.

In some embodiments, the sampler system includes at least two springs. A first spring attaches the adsorptive sampler to the top face of the cylindrical enclosure and a second spring attaches the adsorptive sampler to the bottom face of the cylindrical enclosure.

In some embodiments, the first spring and the second spring are mounted opposite to one another between the top and bottom faces of the cylindrical enclosure.

In some embodiments, the first spring is attached to a leftmost surface on the top face of the cylindrical enclosure and the second spring is attached to a rightmost surface on the bottom face of the cylindrical enclosure.

In some embodiments, the adsorptive sampler is mounted diagonally between the first spring and the second spring.

In some embodiments, the bottom face of the cylindrical enclosure has a flat impermeable platform concentric with an axis of the cylindrical enclosure and having a surface area no more than one half of a surface area of the bottom face to which the spring is attached.

In some embodiments, the top face of the cylindrical enclosure has a hook mounted at a focus of the top face which connects the flotation device to the cylindrical enclosure with the cable.

In some embodiments, the rigid film is substantially rectangular.

In some embodiments, the flat impermeable platform is substantially cylindrical.

In some embodiments, the cantilever has a height from 0.4 to 0.8 times a height of the cylindrical enclosure.

In some embodiments, the adsorptive sampler has a widest diameter that is from 1.5 to 3.5 times greater than a thickness of the cantilever.

In some embodiments, the cantilever is mounted to the flat impermeable platform equidistant between a first end of the flat impermeable platform and a second end of the flat impermeable platform.

In some embodiments, the first spring has a first stiffness which is different than a second stiffness of the second spring.

In some embodiments, the first spring has a first stiffness which is same as a second stiffness of the second spring.

In some embodiments, a length of the cantilever in a longest dimension is from 1.5 to 2.5 times greater than a widest diameter of the adsorptive sampler.

In some embodiments, the cantilever is attached to the bottom face of the cylindrical enclosure.

The foregoing general description of the illustrative present disclosure and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
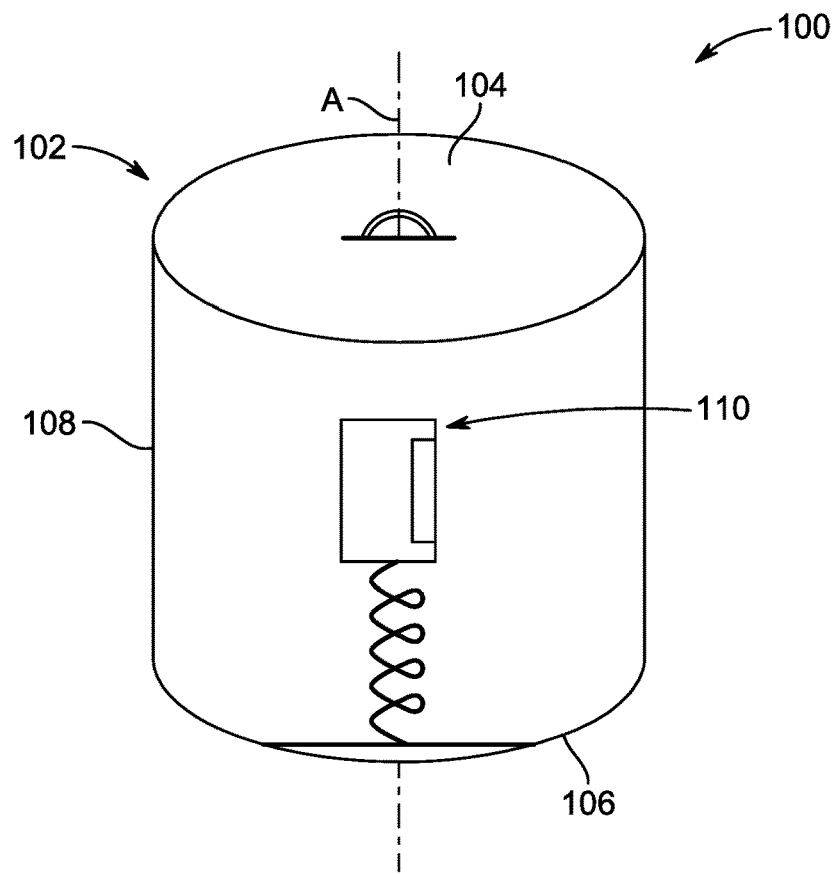
FIG. 1 is a schematic perspective view of a sampler system for water contaminants, according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values there between.

The term "adsorbent" hereafter and in the claims is defined as any material that adsorbs, wherein adsorbs or adsorption may be defined as the adhesion of atoms, ions, biomolecules or molecules of gas, liquid, or dissolved solids to a surface. This process creates a film of the adsorbate (the atoms, ions, or molecules being accumulated) on the surface of the adsorbent. Adsorption is therefore a surface phenomenon, and so can be used to take up said adsorbate and then to release or substantially release the adsorbate for laboratory analysis by known processes such as contact by a leaching liquid.

Samplers and preferably real-time sensors may be provided singly or in groups, and may be installed in the environmental medium, or in a location where they will at least intermittently contact the environmental medium (for example, with tides, increased flow in a sewer, or other changes in the medium). Installation may comprise attachment to or containment in a box or other container that has apertures so that the medium will reach the sampler/sensors. Installation may be on a flexible elongate member such as cable (including strings, cords, chains), on a rigid or generally rigid elongated member (such as a bar, board, post, hanger), and/or hanging down on a flexible, rigid, or generally rigid member from a support base. Support bases may comprise, for example, a buoy including any floating object, or a fixed or usually fixed member such as a manhole cover, upstanding pipe, pier, bridge, tree, smokestack, or other infrastructure or building portion. Support bases may include telemetry and/or GPS in some embodiments. The term "telemetry base" is also used herein and refers to apparatus that is distanced from the sampler and real-time sensor, for example, to receive signals transmitted from the real-time sensors. A telemetry base is not necessarily physically connected to, supporting, or holding the sampler and real-time sensor, but is associated with the sampler system at least by operative connection through telemetry signals. A telemetry base, however, may also in certain embodiments be the support base, for example, a buoy that comprises telemetry apparatus and preferably also GPS apparatus, wherein the sampler and/or the real-time sensor are connected to and typically suspended from the buoy.

Aspects of the present disclosure are directed to a sampler system which is inexpensive and as efficient as the active sampling process. The sampler system is developed based on the naturally occurring forces of the water to vibrate or move an adsorptive sampler and hence to enhance pollutant adsorption capacity. The vibrations of the adsorptive sampler increase physical interactions between the adsorptive material and the surrounding fluid, which leads to enhanced physical and chemical adsorption. The sampler system includes an elastic spring element connected to the adsorptive sampler that is subjected to excitation forces that occur naturally in a body of water. The excitation forces are associated with gravity waves, tidal waves, and currents due to temperature changes and the Coriolis effect.

Referring to FIG. 1, a schematic perspective view of a sampler system 100 for water contaminants is illustrated, according to an embodiment of the present disclosure. The sampler system 100 is used for monitoring the quality of water in a water body by detecting contaminants present in the water. In an embodiment, the water body may be a sea, a pond, a lake, or water stored in a container for various commercial or industrial applications. The sampler system 100 includes a cylindrical enclosure 102 having a top face 104, a bottom face 106, and a cylindrical surface 108 extending between the top face 104 and the bottom face 106. In one embodiment, each of the top face 104 and the bottom face 106 may include a flat surface. In another embodiment, each of the top face 104 and the bottom face 106 may include a curved surface. In an embodiment, each of the top face 104 and the bottom face 106 are circular in shape. In an embodiment, the diameter of the top face 104 and the bottom face 106 are the same. In an embodiment, the diameter of the top face 104 is from 0.7 to 0.9 times greater than the diameter of the bottom face 106, preferably 0.8 times greater thus providing a truncated conical shape. In an embodiment, the diameter of the bottom face 106 is from 0.7 to 0.9 times greater than the diameter of the top face 104, preferably 0.8 times greater. In an embodiment, the top face 104 and the bottom face 106 are concentric with one another around an axis 'A' of the cylindrical enclosure 102. In an embodiment, the cylindrical enclosure 102 has a column extending from the top face 104 to the bottom face 106. In an alternate embodiment, the enclosure 102 can be of different shapes, such as spherical, triangular, rectangular, polygonal, or the like. According to the present disclosure, at least the cylindrical surface 108 is fluid-permeable. The term, "fluid-permeable", refers to an ability of a fluid to flow through a boundary, without substantial obstruction. Particularly, the cylindrical surface 108 is made of a screen or a mesh to allow water to flow therethrough. In some embodiments, the top face 104 and the bottom face 106 may be fluid-permeable. In some embodiments, the fluid-permeable material may be a perforate material known in the art, such as low-density polyethylene, high-density polyethylene, polyvinylidene fluoride, and polycarbonate, and porous membranes thereof. In an embodiment, the cylindrical surface 108 has a plurality of pores to allow fluid to flow through it. In an embodiment, the cylindrical surface 108 has a pore size ranging from of from 50 µm to 250 µm preferably 75 µm to 225 µm, preferably 100 µm to 200 µm, preferably 125 µm to 175 µm, or 150 µm. In an embodiment, the top surface 104 and bottom surface 106 contain a plurality of pores to allow a fluid to pass through it. In an embodiment, the top surface 104 and the bottom surface 106 each have a pore size ranging from of from 100 µm to 300 µm preferably 150 µm to 250 µm, or 200 µm. The fluid-permeable material allows water and accompanied pollutants to pass therethrough. The sampler system 100 further includes an adsorptive sampler 110 housed within the cylindrical enclosure 102. In an embodiment, the column extending from the top face 104 to the bottom face 106 surrounds the sampler 110. In an embodiment, the column may be molded integrally with, or otherwise fixed between the top face 104 and the bottom face 106. In an embodiment, the column may be detachable from the platform, for example, by a threaded connection or other fastening device. In an embodiment, a diameter of the column is from 0.2 to 0.6 times the diameter of either the top face 104 or the bottom face 106, preferably from 0.3 to 0.5 times greater, or 0.4 times greater. In an embodiment, the sampler 110 comprises an annular space contains an ion-exchange resin within the annular space. In an embodiment, the sampler 110 includes external, such as a shell, inlets, and fittings, and are made of stainless steel. In an embodiment, an inlet tubing of the sampler 110 is made from polytetrafluoroethylene (PTFE).

Figure 2:
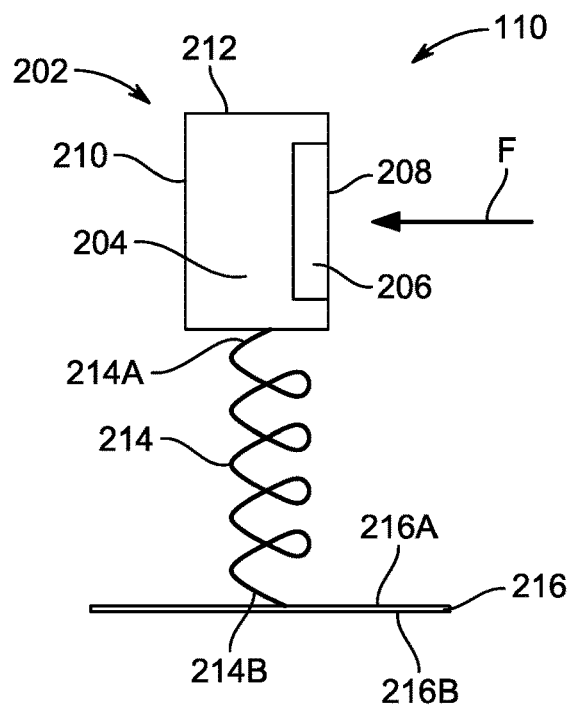
FIG. 2 is a schematic side view of an adsorptive sampler of the sampler system, according to certain embodiments.

Referring to FIG. 2, a schematic side view of the adsorptive sampler 110 is illustrated, according to certain embodiments. The adsorptive sampler 110 includes a housing 202 having a cavity 204 and an adsorptive material 206 disposed inside the cavity 204. The housing 202 of the adsorptive sampler 110 is in the shape of a cylinder. In an embodiment, the housing 202 is in the shape of a cylinder that is axially perpendicular to the axis of the enclosure 102. That is the housing 202 is placed inside enclosure 102 so that the housing 202 is axially perpendicular to axis 'A' of the cylindrical enclosure 102. Particularly, the housing 202 includes a front face 208, a back face 210, and a cylindrical surface 212 extending between the front face 208 and the back face 210. As used herein, the front face 208 can be defined as a front surface that is exposed to naturally occurring forces of water, represented by 'F' in FIG. 2, and allows water to enter though it. The back face 210 can be defined as a back surface that is not exposed to naturally occurring forces of water, represented by 'F' in FIG. 2, but rather is positioned opposite to the front face 208 on the other end of the housing 202. In an embodiment, the cavity 204 has a length in a longest dimension of from 0.1 to 0.4 times a length in a longest dimension of the housing 202, preferably from 0.2 to 0.3 times greater, or 0.25 times greater. In some embodiments, the adsorptive material 206 is at least one selected from the group consisting of activated carbon, silica gel, zirconia, titania, alumina, zeolite, and an ion-exchange resin. In another embodiment, each of the front face 208 and the back face 210 may include a curved surface. In an embodiment, each of the front face 208 and the back face 210 are flat plate in shape. In an embodiment, the length of the front face 208 and the bottom face 106 are the same. In an embodiment, the length of the top face 208 is from 0.7 to 0.9 times greater than the length of the back face 210, preferably 0.8 times greater. In an embodiment, the length of the back face 210 is from 0.7 to 0.9 times greater than the length of the front face 208, preferably 0.8 times greater. In an embodiment, the front face 208 and the back face 210 are concentric with one another around the axis 'A' of the cylindrical enclosure 102. Referring to FIG. 1 and FIG. 2, the housing 202 is disposed within the cylindrical enclosure 102 such that the front and back faces 208, 210 of the housing 202 faces the cylindrical surface 108 of the sampler system 100. Further, the housing 202 of the adsorptive sampler 110 is attached to the cylindrical enclosure 102 using a spring 214. The spring 214 include a first end 214A configured to attach with the housing 202 of the adsorptive sampler 110 and a second end 214B configured to attach with the bottom face 106 of the cylindrical enclosure 102. In one embodiment, the spring 214 may be a compression spring. In some embodiments, the spring 214 may be a flexible element made of a metal, an elastomer, or a polymeric material that may be sensible and flexible to move the adsorptive sampler 110 based on naturally occurring forces of water, represented by 'F' in FIG. 2, when the sampler system 100 is implemented in the water body. In an embodiment, the spring 214 attached to a hook at the first end 214A of the housing 202, so that the spring 214 is removable. In an embodiment, the spring is fixedly attached to the housing 202 so that the spring 214 is integral with the housing 202.

The cylindrical enclosure 102 of the sampler system 100 further includes a flat impermeable platform 216 disposed on the bottom face 106 thereof. Particularly, the flat impermeable platform 216 includes a top surface 216A configured to engage with the second end 214B of the spring 214 and a bottom surface 216B defined in conformance with the bottom face 106 of the cylindrical enclosure 102 such that the flat impermeable platform 216 is disposed on the bottom face 106 intact. The flat impermeable platform 216 may be made of a metal or a polymer material. In one embodiment, the flat impermeable platform 216 may have a circular shape having a surface area no more than one half of a surface area of the bottom face 106, or preferably no more than one quarter of the area of the bottom face 106. In some embodiments, the flat impermeable platform 216 may have an elliptical shape or a polygon shape having a surface area no more than one half of the surface area of the bottom face 106, preferably no more than one quarter of the area of the bottom face 106. The flat impermeable platform 216 is disposed on the bottom face 106 of the cylindrical enclosure 102 in such a manner that a central axis of the flat impermeable platform 216 is concentric with an axis 'A' of the cylindrical enclosure 102. In one embodiment, the flat impermeable platform 216 may be detachably coupled to the bottom face 106 using a press fit mechanism, fastening members, a quick release mechanism, or any other known mechanism that detachably connects the flat impermeable platform 216 with the bottom face 106. In some embodiments, the flat impermeable platform 216 may be permanently attached to the bottom face 106, for example using a welding method or a riveting method.

Figure 3:
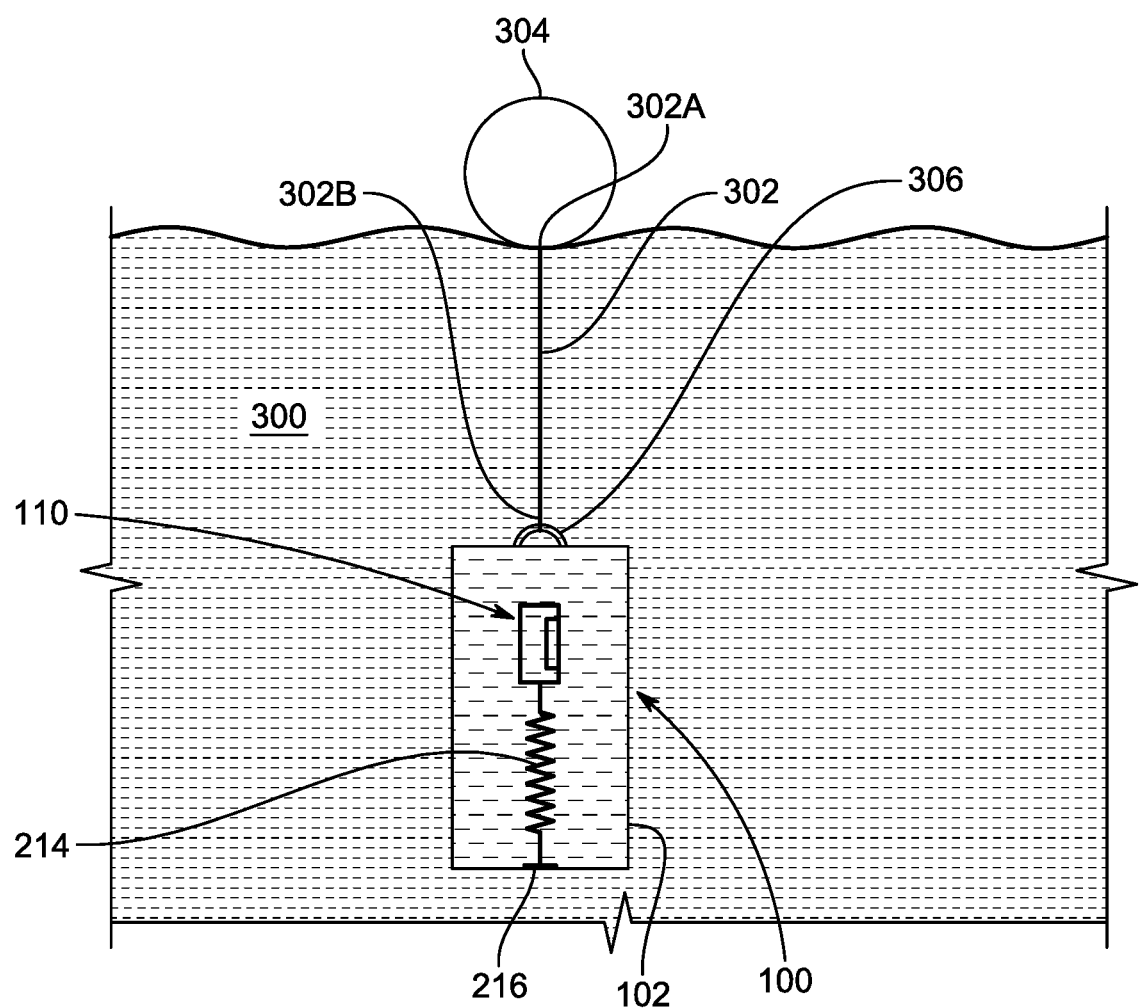
FIG. 3 is a schematic side view of the sampler system of FIG. 1 implemented in a water body, according to certain embodiments.

Referring to FIG. 3, a schematic side view of the sampler system 100 implemented in a water body 300 is illustrated, according to certain embodiments. Referring to FIG. 1 and FIG. 3, the sampler system 100 includes a cable 302 connecting the top face 104 of the cylindrical enclosure 102 to a flotation device 304. In an embodiment, the cable 302 is made of rope, metal, plastic, or a polymer. In an embodiment, a length of the cable 302 is equal to a length of the sampler system 100. In an embodiment, a length of the cable 302 is less than a length of the sampler system 100. The flotation device 304 helps to float the sampler system 100 in the water body 300 at a desired height from a water level. In an embodiment, the flotation device 304 is a buoy or a rigid arm. In an embodiment, the cable 302 is formed integral with the flotation device 304. In an embodiment, the cable 302 is detachable from the flotation device 304. The desired distance of the sampler system 100 from the surface of the water may be set by adjusting a length of the cable 302. A first end 302A of the cable 302 is attached to the flotation device 304 and a second end 302B of the cable 302 is attached to the top face 104 of the cylindrical enclosure 102. Particularly, the top face 104 of the cylindrical enclosure 102 has a hook or attachment fixture 306 mounted at a focus thereof. The hook 306 connects the flotation device 304 to the cylindrical enclosure 102 with the cable 302. In one embodiment, the hook or attachment fixture 306 may be formed integral with the top face 104 of the cylindrical enclosure 102. In another embodiment, the hook or attachment fixture 306 may be an individual component detachably connected to the top face 104 of the cylindrical enclosure 102. In an embodiment, the cable 302 is formed integral with the hook or attachment fixture 306. In an embodiment, the cable 302 is removable from the hook or attachment fixture 306, such as by tying and untying a knot in the rope cable 302. In an embodiment, the hook or attachment fixture 306 is shaped like a semi-circle. In an embodiment, the hook or attachment fixture 306 has the shape of a square, a rectangle, a triangle, or any other polygonal shape. In an embodiment, the hook or attachment fixture 306 is formed of a metal, a plastic, a polymer, or a ceramic. In an embodiment, the flotation device 304 can accommodate multiple cables 302, and each cable 302 holds one sampler system 100. In an embodiment, the flotation device can accommodate from 2 to 8 cables 302, preferably from 3 to 7 cables, or 5 cables 302. In some embodiments, the first end 302A of the cable 302 is attached to the flotation device 304 in such a manner that the desired distance of the sampler system 100 from the surface of the water may be adjusted by pulling or loosening the cable 302 with respect to the flotation device 304.

During an implementation of the sampler system 100 in the water body 300, naturally occurring forces 'F' due to waves or currents act as the excitation forces on the front face 208 of the housing 202 to move the adsorptive sampler 110 in one or more directions. Biasing forces of the spring 214 moves the adsorptive sampler 110 in a direction opposite to the direction of the excitation forces. Thus, the adsorptive sampler 110 experiences a vibrational or periodic motion. Vibration frequency can be selectively chosen or adjusted by selecting a desired combination of a stiffness of the spring 214 and a mass of the adsorptive sampler 110. When the adsorptive sampler 110 moves back and forth to cause vibration thereof, the adsorptive material 206 disposed within the housing 202 of the adsorptive sampler 110 is exposed to increased interaction with the surrounding fluid. Thus, enhanced physical and chemical adsorption is established.

Figure 4:
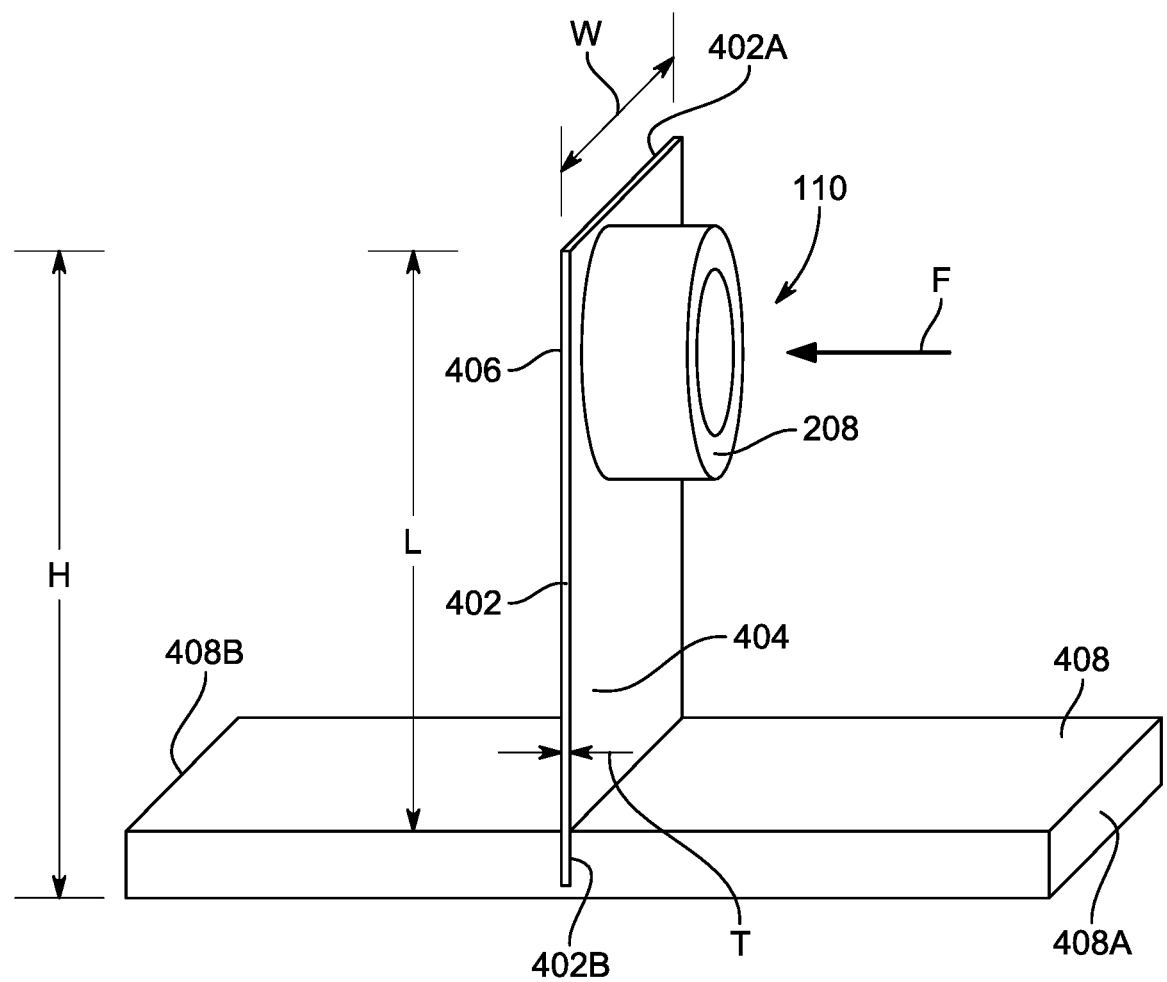
FIG. 4 is a schematic perspective view showing coupling of the adsorptive sampler to a cylindrical enclosure of the sampler system of FIG. 1 using a cantilever, according to certain embodiments.

Referring to FIG. 4, coupling the adsorptive sampler 110 to the cylindrical enclosure 102 using a cantilever 402 is illustrated, according to an embodiment of the present disclosure. The cantilever 402 is attached to the bottom face 106 of the cylindrical enclosure 102 and acts as a leaf spring. In an embodiment, the cantilever 402 is in the form of a rigid film and the rigid film is substantially rectangular. In an embodiment, the cantilever 402 is substantially triangular, substantially circular, or any other polygonal shape. The cantilever 402 is alternatively referred to as 'the rigid film 402'. The rigid film 402 includes a top end 402A configured to couple with the adsorptive sampler 110 and a bottom end 402B configured to engage with the bottom face 106 of the cylindrical enclosure 102. In an embodiment, the rigid thin film 402 is made of metal, plastic, ceramic, a polymer, or the like. The rigid film 402 has a height 'H' extending between the top end 402A and the bottom end 402B and a width 'W' greater than or equal to a widest diameter of the adsorptive sampler 110. In some embodiments, the cantilever 402 has the height 'H' from 0.4 to 0.8 times a height of the cylindrical enclosure 102 defined between the top face 104 and the bottom face 106, preferably from 0.5 to 0.7 times a height, or 0.6 times a height of the cylindrical enclosure 102. The rigid film 402 is connected to the bottom face 106 of the cylindrical enclosure 102 along a flat edge thereof. Particularly, the flat edge of the bottom end 402B of the cantilever 402 is mounted to a flat impermeable platform 408, which is substantially rectangular. In an embodiment, the flat impermeable platform 408 is substantially cylindrical, substantially triangular, or any other polygonal shape. In an embodiment, the cantilever 402 is mounted to the flat impermeable platform 408 equidistant between a first end 408A of the flat impermeable platform 408 and a second end 408B of the flat impermeable platform 408. In an embodiment, the flat impermeable platform 408 is made of a metal, a plastic, or a ceramic. The platform is preferably of substantial mass and represents a majority of the mass of the sampler system 100. The mass of the platform helps ensure correct orientation of the housing and functions to keep the sampler system at a desired depth. In an embodiment, the cantilever 402 is not equidistant between the first end 408A and the second end 408B. In an embodiment, the cantilever 402 is mounted closer to the first end 408A, so that a distance between the cantilever 402 and the first end 408A is from 0.2 to 0.5 times greater than a distance between the cantilever 402 and the second end 408B, preferably from 0.3 to 0.4 times greater, or 0.33 times greater. In an embodiment, the cantilever 402 is mounted closer to the second end 408B, so that a distance between the cantilever 402 and the second end 408B is from 0.2 to 0.5 times greater than a distance between the cantilever 402 and the first end 408A, preferably from 0.3 to 0.4 times greater, or 0.33 times greater. The adsorptive sampler 110 is attached to at least one surface of the rigid film 402 by the back face 210 and positioned distal to the bottom face 106 of the cylindrical enclosure 102. Particularly, the rigid film 402 includes a first surface 404 configured to engage with the adsorptive sampler 110 and a second surface 406 distal to the first surface 404. In an embodiment, the adsorptive sampler 110 is formed integral with the rigid film 402. In an embodiment, the adsorptive sampler is removable from the rigid film 402. The first surface 404 of the rigid film 402 is configured to engage with the back face 210 of the adsorptive sampler 110. The rigid film 402 has a thickness 'T' extending between the first surface 404 and the second surface 406. In some embodiments, the widest diameter of the adsorptive sampler is from 1.5 to 3.5 times greater than the thickness 'T' of the cantilever 402, preferably from 2 to 3 times greater, or 2.5 times greater. In some embodiments, a length 'L' of the cantilever 402 in a longest dimension is from 1.5 to 2.5 times greater than the widest diameter of the adsorptive sampler 110, preferably from 1.75 to 2.25 times greater, or 2 times greater. The length 'L' of the cantilever 402 may be defined as a distance between the top end 402A of the cantilever 402 and a top surface of the flat impermeable platform 216. The dimensional specifications such as the length 'L' and the thickness 'T' of the cantilever 402 and the height 'H' of the cantilever 402 with respect to the height of the cylindrical enclosure 102 may be defined based on water current, otherwise known as the naturally occurring forces 'F' exerted by the water on the front face 208 of the adsorptive sampler 110. The length 'L', the width 'W', the thickness 'T', and the height 'H' of the cantilever 402 may be defined to set a desired stiffness for the cantilever 402 corresponding to a desired vibrational motion of the adsorptive sampler 110 to establish enhanced level of pollutant adsorption. In an embodiment, the height of the cantilever 402 is from 1.1 to 1.5 times greater than the length of the cantilever 402, preferably from 1.2 to 1.4 times greater, or 1.3 times greater. In an embodiment, the rigid film 402 is fastened to the flat impermeable platform 408 by a fastening or screwing means, such as hinges, screws, or the like.

Figure 5A:
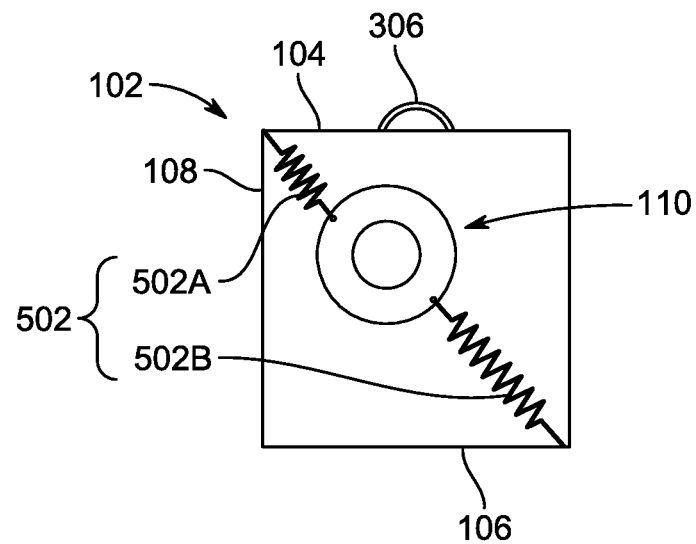
FIG. 5A is a schematic side view showing coupling of the adsorptive sampler to the cylindrical enclosure of the sampler system of FIG. 1 using a pair of springs, according to certain embodiments.
Figure 5B:
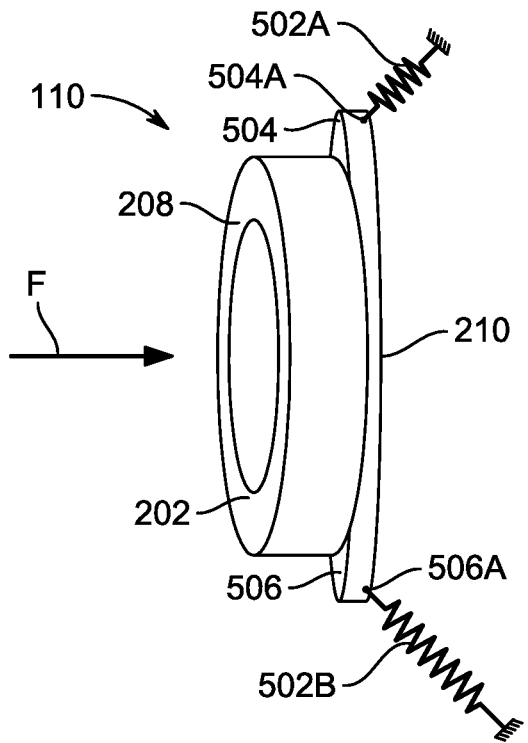
FIG. 5B is a schematic perspective view of the adsorptive sampler showing coupling thereof with the cylindrical enclosure using the pair of springs of FIG. 5A, according to certain embodiments.

Referring to FIG. 5A, a schematic side view of the sampler system 100 having the adsorptive sampler 110 attached to the cylindrical enclosure 102 using a pair of springs 502 is illustrated, according to an embodiment of the present disclosure. The pair of springs 502 includes a first spring 502A configured to attach the adsorptive sampler 110 to the top face 104 of the cylindrical enclosure 102 and a second spring 502B configured to attach the adsorptive sampler 110 to the bottom face 106 of the cylindrical enclosure 102. In an embodiment, the first spring 502A and the second spring 502B are compression springs. In some embodiments, the first spring 502A and the second spring 502B may be a flexible element made of a metal, an elastomer, or a polymeric material. In an embodiment, the first spring 502A and the second spring 502B are substantially the same as spring 214. In some embodiments, the first spring 502A has a first stiffness which is different than a second stiffness of the second spring 502B. In an embodiment, the first stiffness is from 0.4 to 0.9 times greater than the second stiffness, preferably from 0.5 to 0.8 times greater, preferably from 0.6 to 0.7 times greater, or 0.65 times greater. In an embodiment, the second stiffness is from 0.4 to 0.9 times greater than the first stiffness, preferably from 0.5 to 0.8 times greater, preferably from 0.6 to 0.7 times greater, or 0.65 times greater. In some embodiments, the first stiffness of the first spring 502A is same as the second stiffness of the second spring 502B. The first spring 502A and the second spring 502B are attached to the adsorptive sampler 110 diametrically opposite to each other, as shown in FIG. 5B. Further, the first spring 502A and the second spring 502B are mounted opposite to one another between the top and bottom faces 104, 106 of the cylindrical enclosure 102. When the first stiffness of the first spring 502A is different from the second stiffness of the second spring 502B, construction geometry of the adsorptive sampler 110 becomes asymmetric, which biases the vibrational motion of the adsorptive sampler 110. In an embodiment, the first spring 502A and the second spring 502B are mounted on a same side of the cylindrical enclosure 102 between the top face 104 and the bottom face 106. In an embodiment, the first spring 502A and the second spring 502B are both mounted towards the top face 104 of cylindrical enclosure 102 on opposite sides of the adsorptive sampler 110. In an embodiment, the first spring 502A and the second spring 502B are both mounted towards the bottom face 106 of cylindrical enclosure 102 on opposite sides of the adsorptive sampler 110.

FIG. 5B illustrates coupling of the adsorptive sampler 110 with the pair of springs 502 (first spring 502A and second spring 502B). Particularly, the back face 210 of the housing 202 of the adsorptive sampler 110 includes a first flange 504 having a first aperture 504A and a second flange 506 having a second aperture 506A. The second flange 506 is disposed diametrically opposite to the first flange 504. In an embodiment, each of the first flange 504 and second flange 506 are fabricated or a metal or a plastic. In an embodiment, each of the first flange 504 and second flange 506 are formed integral with the back face 210 of the adsorptive sampler 110. In an embodiment, each of the first flange 504 and second flange 506 are removable from the back face 210 of the adsorptive sampler 110. Each of the first aperture 504A and the second aperture 506A is configured to couple with one end of each of the first and second springs 502A, 502B, respectively. In an embodiment, each of the first aperture 504A and the second aperture 506A have a diameter that is of from 0.3 to 0.5 times a width of the back face 210, preferably 0.4 times the width of the back face 210. Referring to FIG. 5A and FIG. 5B, the first spring 502A is attached to a leftmost surface on the top face 104 of the cylindrical enclosure 102 and the second spring 502B is attached to a rightmost surface on the bottom face 106 of the cylindrical enclosure 102, as such the adsorptive sampler 110 is mounted diagonally between the first spring 502A and the second spring 502B. Particularly, another end of each of the first and second springs 502A, 502B is detachably coupled to the top and bottom faces 104, 106 of the cylindrical enclosure 102. In some embodiments, the first spring 502A may be attached to the rightmost surface on the top face 104 of the cylindrical enclosure 102 and the second spring 502B may be attached to the leftmost surface on the bottom face 106 of the cylindrical enclosure 102. In some embodiments, the first spring 502A may be attached to a center surface on the top face 104 of the cylindrical enclosure 102 and the second spring 502B may be attached to a center surface on the bottom face 106 of the cylindrical enclosure 102.

Figure 6:
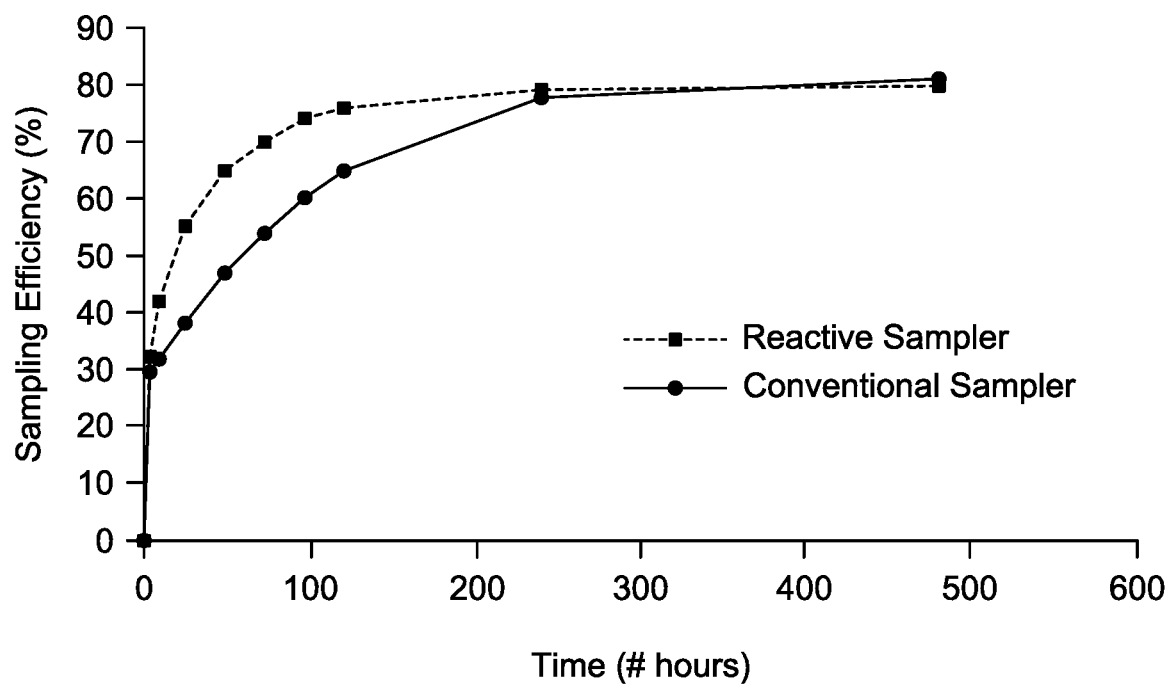
FIG. 6 is a graphical representation comparing sampling efficiency of the conventional sampler and the sampler system of FIG. 1, according to certain embodiments.

According to the present disclosure, the sampler system 100 includes the adsorptive sampler 110 disposed within the cylindrical enclosure 102 using the spring 214, the cantilever 402, and the pair of springs 502, according to various embodiments. The adsorptive sampler 110 utilizes the naturally occurring forces 'F' of the water to vibrate (e.g., react to naturally occurring waterborne forces), thereby enhancing the pollutant adsorption capacity and/or rate or pollution adsorption thereof. The vibrations/movements of the adsorptive sampler 110 further increases the physical interactions between the adsorptive material 206 and the surrounding fluid, which further leads to enhanced physical and chemical adsorption. As shown in FIG. 6, sampling efficiency of reactive sampler system 100 of the present disclosure is higher than that of a conventional fixed sampler, which indicates that the sampler system 100 of the present disclosure is capable of capturing more contaminants by the mechanism of adsorption. Simple construction and fewer components make the sampler system 100 of the present disclosure less expensive, while making the sampler system 100 more efficient with the help of spring arrangement and the naturally occurring forces of the water.

Numerous modifications and variations of the present disclosure are possible in light of the above teachings. It is therefore to be understood that within the scope of the appended claims, the invention may be practiced otherwise than as specifically described herein.

The invention claimed is:

1. A sampler system for water contaminants, comprising:
an adsorptive sampler housed within a cylindrical enclosure, wherein the cylindrical enclosure has a top face, a bottom face and a cylindrical surface, wherein at least the cylindrical surface is fluid-permeable;
a cable connecting the top face of the cylindrical enclosure to a flotation device; and
a spring connecting the adsorptive sampler to the bottom face of the cylindrical enclosure;
wherein the adsorptive sampler comprises a housing having a cavity, and an adsorptive material disposed inside the cavity, and
wherein the housing is attached to the spring, the housing having a front face and a back face.

2. The system of claim 1, wherein the fluid-permeable cylindrical surface is a screen or a mesh; and
the adsorptive material is at least one selected from the group consisting of activated carbon, silica gel, zirconia, titania, alumina, zeolite, and ion-exchange resins.

3. The system of claim 1, wherein the spring is a cantilever in the form of a rigid film, wherein the rigid film is connected to the bottom face of the cylindrical enclosure along a flat edge of the rigid film.

4. The system of claim 3, wherein the adsorptive sampler is attached to at least one surface of the rigid film by the back face; and
the adsorptive sampler is positioned distal to the bottom face of the cylindrical enclosure.

5. The system of claim 4, wherein the housing of the adsorptive sampler is in the form of a cylinder.

6. The system of claim 3, wherein the rigid film is substantially rectangular.

7. The system of claim 3, wherein the cantilever has a height from 0.4 to 0.8 times a height of the cylindrical enclosure.

8. The system of claim 3, wherein the adsorptive sampler has a widest diameter that is from 1.5 to 3.5 times greater than a thickness of the cantilever.

9. The system of claim 3, wherein a length of the cantilever in a longest dimension is from 1.5 to 2.5 times greater than a widest diameter of the adsorptive sampler.

10. The system of claim 3, wherein the cantilever is attached to the bottom face of the cylindrical enclosure.

11. The system of claim 1, comprising at least two springs, a first spring attaching the adsorptive sampler to the top face of the cylindrical enclosure and a second spring attaching the adsorptive sampler to the bottom face of the cylindrical enclosure.

12. The system of claim 11, wherein the first spring and the second spring are mounted opposite to one another between the top and bottom faces of the cylindrical enclosure.

13. The system of claim 12, wherein the first spring is attached to a leftmost surface on the top face of the cylindrical enclosure and the second spring is attached to a rightmost surface on the bottom face of the cylindrical enclosure.

14. The system of claim 13, wherein the adsorptive sampler is mounted diagonally between the first spring and the second spring.

15. The system of claim 13, wherein the first spring has a first stiffness which is different than a second stiffness of the second spring.

16. The system of claim 13, wherein the first spring has a first stiffness which is the same as a second stiffness of the second spring.

17. The system of claim 1, wherein the bottom face of the cylindrical enclosure has a flat impermeable platform concentric with an axis of the cylindrical enclosure and having a surface area no more than one half of a surface area of the bottom face to which the spring is attached.

18. The system of claim 17, wherein the flat impermeable platform is substantially cylindrical.

19. The system of claim 17, wherein a cantilever is mounted to the flat impermeable platform equidistant between a first end of the flat impermeable platform and a second end of the flat impermeable platform.

20. The system of claim 1, wherein the top face of the cylindrical enclosure has a hook mounted at a center of the top face which connects the flotation device to the cylindrical enclosure with the cable.

* * * * *